United States Patent
Wilhelmsen et al.

(10) Patent No.: US 12,055,468 B2
(45) Date of Patent: *Aug. 6, 2024

(54) DEVICES, SYSTEMS AND METHODS FOR MICROBIAL SAMPLING OF FROZEN PRODUCTS

(71) Applicant: Fremonta Corporation, Fremont, CA (US)

(72) Inventors: Eric Wilhelmsen, Fremont, CA (US); Yongqing Huang, Fremont, CA (US); Florence Wu, Fremont, CA (US); Garth Hoffmann, Fremont, CA (US); Wei Wu, Fremont, CA (US)

(73) Assignee: Fremonta Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/898,178

(22) Filed: Aug. 29, 2022

(65) Prior Publication Data
US 2022/0412850 A1    Dec. 29, 2022

Related U.S. Application Data

(63) Continuation of application No. 17/570,144, filed on Jan. 6, 2022.
(Continued)

(51) Int. Cl.
*G01N 1/02* (2006.01)
*G01N 1/40* (2006.01)
*G01N 33/02* (2006.01)

(52) U.S. Cl.
CPC ............. *G01N 1/4022* (2013.01); *G01N 1/02* (2013.01); *G01N 1/405* (2013.01); *G01N 33/02* (2013.01); *G01N 2001/028* (2013.01)

(58) Field of Classification Search
CPC ........ G01N 1/4022; G01N 1/02; G01N 1/405; G01N 33/02; G01N 2001/028; G01N 1/14; G01N 2001/149; G01N 2033/1873
(Continued)

(56) References Cited

U.S. PATENT DOCUMENTS

| 4,799,379 A | * | 1/1989 | Suga ................. G01N 21/8483 73/170.19 |
| 5,476,794 A | * | 12/1995 | O'Brien ................. G01V 9/007 422/534 |
| 2022/0214255 A1 | * | 7/2022 | Wilhelmsen ............. G01N 1/02 |

FOREIGN PATENT DOCUMENTS

| CN | 202682838 U | * | 1/2013 | |
| CN | 108956232 A | * | 12/2018 | ............... G01N 1/28 |

(Continued)

*Primary Examiner* — Robert R Raevis
(74) *Attorney, Agent, or Firm* — Kilpatrick Townsend & Stockton LLP

(57) ABSTRACT

Sampling probe devices, systems and methods for sampling frozen or solid meltable products. Such systems can include a heating element for placing against the frozen or solid product and a sampler with a cover fabricated at least partly from a microbial sampling medium so the cover absorbs a liquid sample from the product. Methods of sampling include heating the product and contacting the product with the cover until sufficient liquid sample is absorbed by the cover of the sampler. The cover can be weighed after sampling and compared to a before-sampling weight to confirm sufficient liquid was obtained. The sample can be tested as an aggregate sample that is representative of the lot or batch of product being sampled, including testing without an enrichment procedure. Systems utilizing automated heated-sampling plates and radiative heaters are also described.

22 Claims, 17 Drawing Sheets

Related U.S. Application Data

(60) Provisional application No. 63/134,671, filed on Jan. 7, 2021.

(58) Field of Classification Search
USPC ........... 73/863, 863.11, 863.12, 864.71, 864, 73/864.91; 374/45; 426/144, 232, 233
See application file for complete search history.

(56) References Cited

FOREIGN PATENT DOCUMENTS

| | | | | |
|---|---|---|---|---|
| CN | 110426244 A | * | 11/2019 | |
| WO | WO-2016141405 A1 | * | 9/2016 | ................ B01L 3/04 |

* cited by examiner

DEVICES, SYSTEMS AND METHODS FOR MICROBIAL SAMPLING OF FROZEN PRODUCTS

CROSS-REFERENCES TO RELATED APPLICATIONS

This application is a Continuation of U.S. application Ser. No. 17/570,144, filed Jan. 6, 2022, which is a Non-Provisional of and claims the benefit of priority of U.S. Provisional Application No. 63/134,671 filed Jan. 7, 2021, which is incorporated by reference herein in its entirety.

This application is generally related to U.S. Patent Publication Nos.: 2020/0030722 entitled "Method and Apparatus for Applying Aggregating Sampling" filed Jul. 29, 2019; 2019/0049419 entitled "Method and Apparatus for Applying Aggregating Sampling to Food Items" filed Aug. 8, 2018; and U.S. Pat. No. 10,663,446 entitled " Methods, System and Devices for Batch Sampling" issued May 26, 2020; each of which is incorporated herein by reference in its entirety for all purposes.

BACKGROUND OF THE INVENTION

The present invention is directed to a method and devices for sampling a frozen or other meltable solid material, such as frozen food.

Many materials including foods are stored and shipped while frozen or in another solid state. This is particularly common for perishable food materials. While in commerce, it is often desirable to sample these materials, such as for microbial testing. However, the frozen or solid-state of the materials renders sampling difficult. The two options generally considered for sampling of these materials are either thawing or melting the material or cutting the frozen or solid material by some means. Each of these approaches has considerable drawbacks and limitations.

Thawing or melting of frozen or solid material requires energy input and time to affect the phase change. Further, the thawing of foods may result in substantial quality losses. The thawing often releases water that damages the packaging making the product unacceptable for anything but immediate use. This is enough of a problem that some industries have developed equipment to commence processing of the product while still in a frozen state.

Cutting frozen or solid materials for sampling presents significant issues and concerns regarding safety. The cutting process inherently involves devices that can injure the sampler. This process can also be damaging to packaging. The potential to add foreign material to the remaining product by the cutting process is also a concern.

Thus, there is a need for improved methods and devices for sampling of frozen or solid products that overcome the challenges noted above.

BRIEF SUMMARY OF THE INVENTION

The present invention is directed to a method and devices for sampling a frozen or other meltable material including frozen foods.

In one aspect, the invention pertains to a sampling method for sampling a frozen or meltable solid product. Such methods can include: heating a sampling probe to an elevated temperature that is greater than a melting point of the frozen or solid product, wherein the sampling probe includes a cover having sampling medium; contacting the sampling probe to a surface of the product, thereby transiently melting the surface of the product with the sampling probe; and absorbing a melted liquid from the surface with the sampling medium of the sampling probe, thereby obtaining a liquid sample from the product without thawing or melting of the entire product. Heating of the sampling probe can be performed by one or more heating elements that can include any of: a resistive electrical heating element; a recirculated heated liquid system; a chemical heating unit or packet; and a solid or liquid fuel combustion unit. In some embodiments, the probe can utilize radiant energy or any combination of heating elements described herein. The sampling method can further include moving the sampling probe so as to contact the surface of the product at multiple locations, thereby obtaining an aggregate sample that is representative of the entire product being sampled. After sampling, the user removes the sampling medium from the probe for testing of the sampling medium for an analyte of interest.

The sampling methods can include verification that suitable liquid sample was obtained. In some embodiments, verification entails weighing the sampling medium after removal from the probe to determine an after-sample weight of the sample medium; and determining whether sufficient sample was collected based on a comparison of the after-sample weight to a standard or measured pre-sample weight of the sample medium.

The methods can further include subsequently testing the sample medium according to a desired testing protocol. In some embodiments, sample testing includes extracting the liquid sample from the sample medium, cleaning and concentrating the liquid sample and performing detection for the analyte of interest without enrichment.

In another aspect, the invention pertains to methods of sampling a frozen or solid product using a cover or sleeve on a heated sampling probe. Such methods can include: placing a sterile sampling medium over a heating element of a heated sampling probe. The sampling medium can be a cover or sleeve having a pocket or opening that fits over the probe. The probe is heated to an elevated temperature above the melting point of the product. The user than contacts a surface of the frozen or solid product with the heated probe such that the sampling medium absorbs melted product or associated liquid from the product during sampling. The user then removes the sampling medium cover from the heated probe. The sampling medium can be a portion of or the entire cover or sleeve that fits over the heating element. In some embodiments, before sampling, the user initially removes the sterilized cover or sleeve from a sealed bag in which it was provided. After sampling, the user can place the cover or sleeve within the bag and seal for subsequent testing of the sample. In some embodiments, the user associates identifying information regarding the product being sampled with identifying information of the sampling medium provided on or attached to the bag. Associating identifying information can include reading or scanning a barcode on the product and a barcode on the sample bag such that the identifying information is received within a tracking system and the sample and product being sample are associated within the tracking system.

In another aspect, the invention pertains to methods of aggregate sampling. Such methods can include: contacting a sample medium to a surface of a product to be sampled to absorb a liquid on the surface with the sample medium; weighing the sampling medium after sampling to determine an after-sample weight of the sample medium; and determining whether sufficient liquid sample was collected by the sample medium based on a comparison of the after-sample weight to a pre-sample weight of the sample medium. The before-sampling weight can be a standard weight or can be measured. The user then tests the sample medium for an analyte of interest. Testing can include use of an extraction and concentration procedure that does not require enrichment.

In yet another aspect, the invention pertains to a heated sampling probe for sampling of a frozen or solid product that is meltable. The probe includes one or more heating elements configured to heat to an elevated temperature above a melting point of the product being sampled; and a sample material cover or sleeve that includes: at least a portion having an absorbent sampling medium and a pocket formed therein for receiving a sampling tool or appendage. In some embodiments, the one or more heating elements are configured for heating by resistive electrical heating. In some embodiments, the one or more heating elements are configured for heating by a recirculated heated liquid system. In some embodiments, the one or more heating elements are configured for heating by a chemical heating unit or packet. In some embodiments, the one or more heating elements are configured for heating by a solid or liquid fuel combustion unit. In some embodiments, the probe can utilize radiant energy or any combination of heating elements described herein. The one or more heating elements are configured to heat to an elevated temperature above the melting point of the product being sampled, typically between 50° C. and 100° C. In some embodiments, the one or more heating elements are configured with a thermostat for maintaining the elevated temperature at a set temperature or a range.

In some embodiments, the sampling material cover includes a liner that is impervious to the melted liquid between the heating element and the sampling medium. The probe itself can be defined as a glove to be worn by a sampling personnel, the glove having the one or more heating elements attached thereon. The sampling medium cover can be defined as an outer glove liner or mitten that fits over the glove. The heating element can be a flexible heating element so as to conform to the shape of the glove and/or the product being sampled. The cover can include an internal liner that is impervious to the melted liquid between the heating element and the sampling medium. In some embodiments, the sampling medium comprises the entire outer surface of the cover. In some embodiments, the sampling medium comprises only a portion of the outer surface of the cover. In some embodiments, the one or more heating elements are electrical resistive heating elements that are electrically coupled to a portable battery.

In some embodiments, the heating elements are powered by a portable power source, such as a battery. The portable power source can be supported within a portable cart to allow sampling personnel to move the cart and sample at any desired location on-site. In some embodiments, the portable cart further includes an identifying means, such as an optical scanner, for obtaining identifying information of the product being sampled and/or the sample medium. The portable cart can also include a computer having a user interface that accesses a tracking system for associating identifying information of the product being sampled and the sample medium. The portable cart can further include a weighing system for determining an after-sample weight of the sample medium.

In another aspect, the invention pertains to sampling system that is at least partly automated in regard to heating and/or sampling of the frozen or solid product. Such systems can include a frame disposed atop a sampling station surface configured to accommodate an open box of a frozen product and a movable assembly supporting a sampling plate having a sampling medium mounted on a surface thereof. In some embodiments, the assembly is movable relative the frame in a downward direction so as to contact the sampling medium with an exposed surface of the frozen product. A heating element is thermally coupled with the sampling plate so as to heat the sampling plate to a desired temperature to thaw the exposed surface of the food product during sampling. In some embodiments, the sampling system can include a vibration motor coupled to the sampling plate to impart vibrations to the sampling plate to facilitate sampling. The system can further include a plurality of springs and dampening mechanisms between the sampling plate and the frame so as to isolate vibrations from the support frame during sampling. In some embodiments, the system further includes a weight sensor coupled to the sampling station surface to monitor a weight of the open box of frozen product. In some embodiments, the frame and sampling station surface are disposed on a mobile cart.

In another aspect, the invention pertains to a sampling method that can include steps of: heating a sampling plate with a heating element so as to heat the sampling plate to a desired temperature to thaw the exposed surface of the food product during sampling; moving a sampling plate mounted on an assembly supported by a frame toward an open box of frozen product disposed on a sampling surface, a sampling medium being mounted on the surface and the assembly being movable relative the frame in a downward direction to contact the sampling medium to the exposed surface of the frozen product; and removing the sampling medium for subsequent testing. In some embodiments, the method further includes the step of: vibrating the sampling plate with a vibrating motor while contacting the product surface with the sampling medium to facilitate sampling.

In yet another aspect, the invention pertains to a sampling system defined by a heated-vibration table having a sampling station surface for placing a frozen product to be sampled thereon. A sampling medium is removably mounted on the sampling station surface and the frozen product is placed to contact the sampling medium. The table includes a heating element thermally coupled with the sampling station surface for thawing the frozen product engaged with the sampling station surface through the sampling medium and a vibrating motor can be used to impart vibrations to the sampling station surface to facilitate sampling. In some embodiments, the heated-vibration table can be included in a mobile cart.

In still another aspect, the invention pertains to a sampling method having steps of: heating a sampling plate with a heating element so as to heat the sampling plate to a desired temperature to thaw the exposed surface of the food product during sampling; placing the exposed surface of the food product on a sampling medium disposed on the sampling plate; vibrating the sampling plate with a vibrating motor while contacting the product surface with the sampling medium to facilitate sampling; and removing the sampling medium from the sampling station surface for subsequent testing.

In another aspect, the invention pertains to a sampling system that includes: a frame disposed atop a sampling station surface configured to accommodate an open box of a frozen product; one or more radiative heaters supported by the frame above the sampling station surface so as to thaw an exposed product surface in the open box when disposed on the sampling station surface; and a sampling medium disposed on a movable plate or a manual sampling tool configured for contacting the exposed product surface for sampling. In some embodiments, the one or more radiative heaters comprise an array of heat lamps. In other embodiments, the one or more radiative heaters comprise one or more quartz heaters, which are particularly suited for linear heating. In some embodiments, these features can be included in a mobile cart.

In yet another aspect, the invention pertains to a sampling method including steps of: heating an exposed surface of a frozen food product disposed on a sampling station surface by one or more radiative heating elements suspended above the sampling station surface, thereby thawing the exposed product surface; contacting the thawed exposed surface of the food product with a sampling medium disposed on a plate and/or a probe thereby obtaining a sample from the exposed surface; and removing the sampling medium from the plate and/or probe for subsequent testing. In some embodiments, the method can further include monitoring a temperature of the exposed product surface with a non-contact temperature sensor, such as by infrared temperature sensing. In some embodiments, the sampling can be performed by an automated function by a sampling medium mounted on a plate of a movable assembly. In other embodiments, the sampling can be performed manually, such as by a manually applied sampling medium or sampling probe having a sampling cover attached thereto.

DETAILED DESCRIPTION OF THE INVENTION

Figure 1:
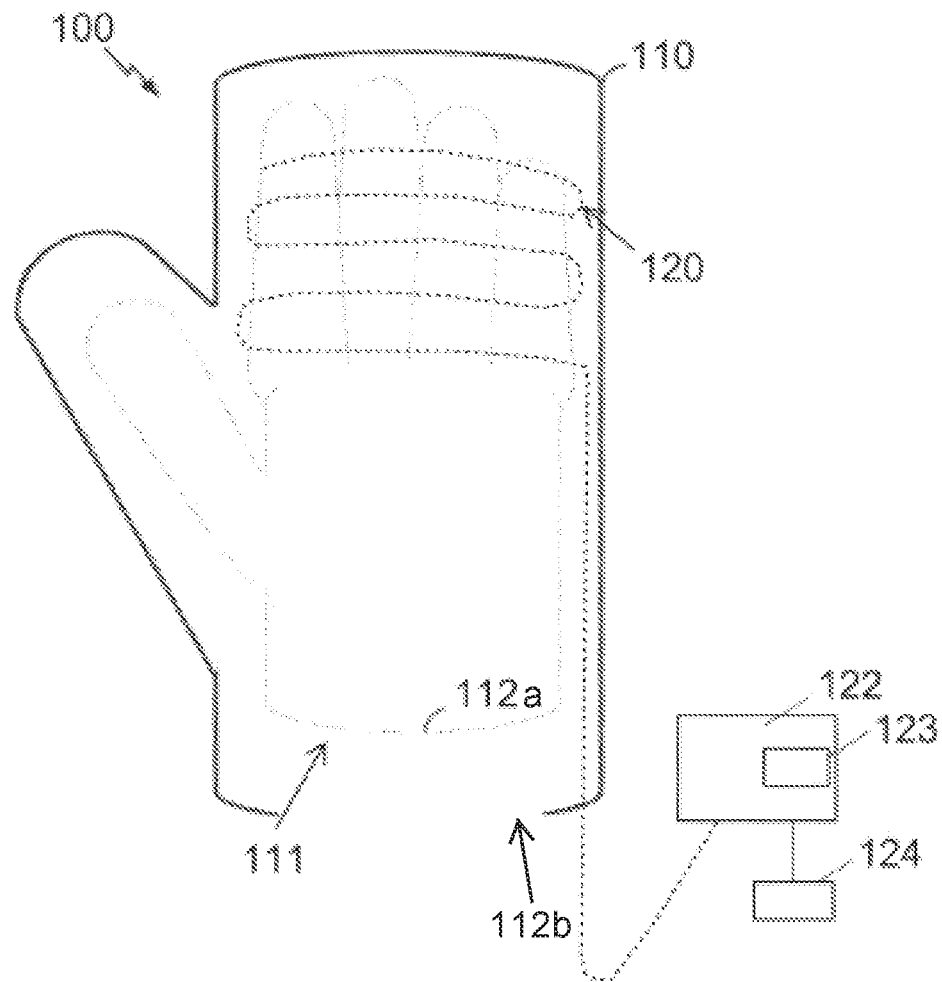
FIG. 1 shows a heated sampling device formed as a glove in accordance with some embodiments of the invention.

Sampling is inherently a proposition of selecting a portion of a material to represent the whole. Classically, a portion of the material is simply collected either by collecting small portions when the material is in multiple distinct pieces as for commodities such as most vegetables, grains, nut meats, fruit or excising a portion from a solid material. Liquids are easiest to sample as aliquots can be easily taken and there is generally more homogeneity. Many products are cut during processing providing the opportunity to collect smaller units of product allowing a more diverse sample to be collected. The sampling of beef trims is an example where excision has been the norm.

Sampling can be used to provide material for a wide range of tests from a wide range of materials. Analytes can be biological such as yeast, molds, bacteria, or viruses. Testing can be used to test attributes of the material itself such as sugar content, acidity, or specific constituents of the material. These attributes can be used for authentication. Analytes can be chemical such as contaminants or foreign materials. The range of analytes that are analyzed by taking samples is large and well known.

Recently, aggregated surface sampling has become an attractive alternative to traditional grab samples. Examples of aggregated surface sampling are described further in U.S. Patent Publications 2020/0030722; 2019/0049419; and U.S. Pat. No. 10,663,446, the entire contents of which are incorporated herein by reference. This technique can provide more representative samples. Unfortunately, these conventional aggregating surface sampling approaches, as described, will not work directly on frozen materials. Therefore, a new method is needed to address this special class of materials.

I. Heated Sampling Probe Devices

To sample frozen materials, it is not necessary to completely thaw the material in cases where the surface layer is suitably representative of the whole or where the surface layer is the expected portion of the material expected to contain the target analyte. In general, these are the conditions that prevail when aggregated sampling is effective. Aggregated sampling of a frozen material can be achieved by melting the surface layer and relying on the thermal resistance of the product to maintain the frozen condition of the bulk of the material. The melted surface layer is placed in intimate contact with the aggregated sampling media transferring a portion of the analyte to the sampling media. Thus, this approach allows for surface sampling of the frozen or solid state material without otherwise thawing or melting the material. To aid in using this method, it is appropriate to consider the three factors—namely a source of heat, the sampling medium and the logistics of use.

A. Heat Sources

The energy source for melting is one fundamental aspect of this sampling device and associated method. Thermal energy is the most direct but conceptually other radiant energy such as microwave or light (e.g. visible, infrared, etc.) can be used. Although one may consider the samplers body heat from their hand within a sampling sleeve, this rapidly becomes inadequate particularly when multiple samples are collected in a short period of time. Therefore, heat sources that are compatible with the sampling needs noted above typically include any of: heated or recirculated water, electrical heating, chemical heating, and fuel combustion. The use of each of these energy sources is elaborated below.

With each all these energy sources, it is important to balance the delivery of energy with the need for temperature control. Too much temperature can damage the product and or the analyte. With too little energy, the desired melting of the surface layer for sampling will not be achieved. It may be useful to consider these two constraints as the quality of the energy.

Typically, a frozen product refers to a product with water ice. However, any solid material with a suitable melting point could be sampled by the methods described herein if it can be absorbed on the sampling media and if the absorbed analyte can be analyzed. Focusing on the primary case where water ice is the solid to me melted, delivered temperatures less than 45° C. are amenable to most analytes including most bacteria. Water ice nominally melts at 0° C.

providing a temperature differential window to drive melting. Clearly these temperatures are only indicative, and higher temperatures may be tolerated in some cases with more robust analytes such as when chemical constituents are to be analyzed. The melting point of water ice can be depressed with solutes as freezing point is a colligative property. It should be noted that with higher temperatures the rate of melting will increase allowing faster moment of the sampling media over the surface of the solid or frozen material.

In one aspect, circulated water or other liquid can be used as the heat source. Circulating water or other liquid with a suitable specific heat to transfer energy to the surface of the material to be sampled. Water is generally preferred due to its high specific heat, availability, and low toxicity. The temperature of the liquid can be controlled with a thermostat and reservoir as desired. Clearly other liquids can be used such as oils if there are specific requirements for sampling. One such restriction would be to sample a material with a melting point over 100° C., the boiling point of water. The heated liquid can be pumped through a bladder or other heat exchanging design covered by the sampling media discussed below at a rate sufficient to melt the surface of the solid sufficiently to sample the surface. This device is normally flexible enough to conform to the potentially irregular surface of the material to be sampled but firmer sampling devices can be desirable. Increasing the flow of the liquid will deliver more energy and therefore greater melting. The bladder can be a simple bag or can have a more restricted bath to provide more uniform temperature depending on the need. The configuration needs to be tailored to fit the configuration of the sampling media. System portability may be limited due to electrical power requirements and the mass of the liquid reservoir. However, cart mounting, and battery power can be used to allow sufficient portability. Temperature control can be effective by a temperature-controlled fluid reservoir, and controlling the rate of heated fluid through the device.

In another aspect, the heat source can utilize direct electrical heating. Direct electrical heating can be achieved by embedding electrical resistive heating elements in heat transfer blocks. Temperature control of these elements can be achieved with thermocouples, thermoresistors, mechanical thermostat systems or any suitable means known in the art. In some embodiments, the heating elements or blocks are flexible or can be articulated to allow flexibility to conform to irregular surfaces and/or to fit the configuration of the sampling media. Typically, the electrical power supply can be direct from the electrical grid. In some embodiments, the electrical power source can be a battery to allow some degree of portability, for example, with a cart mounted sampling system.

In yet another aspect, chemical heating can be used as the heart source. Chemical heating such as used in hand warming packets that are in commerce can be used as a heating source. These packets generally rely on the heat of dissolution of a salt to provide heat. Alternatively, the energy release from the oxidation of finely divided iron can also be used to advantage. Similar technology is used for heating food where other sources of energy are inconvenient. These packets are generally activated by rupturing a container within a container to initiate the chemical reaction. Such packets typically provide elevated thermal output for a period of several hours during which sampling can be performed. A packet of this type can be placed in the sampling sleeve to achieve melting to sample the surface of the material. These packets could be single use for one sample or transferred to other sampling media sleeves for additional samples depending on the energy content. The compositions of these packets are well-known and therefore will not be elaborated upon further. It is appreciated that any suitable heat packet could be used. One notable advantage is that this source of energy is complete portability for sampling is desired.

In still another aspect, propane or liquid or solid fuel can be used as a heat source. Propane or liquid fuel are well known as sources of heat. Combustion or catalytic conversion to combustion products will yield energy but generally it is at higher temperatures and may reduce material quality. However, it should be noted that the necessary reductions in energy quality or temperature have been accomplished for hand warming and other uses so the use of these energy sources can be considered if other conditions warrant their use. This approach may also be highly portable as canisters of liquid fuel for combustion are currently widely available (e.g. camping lanterns, blow torches, cooking torches). Hand warmers based on these energy sources are also known and have long been used but have mostly been displaced by chemical packets in recent years for safety and convenience.

In still another aspect, a sampling system can use radiative heating. In some embodiments, the heating element can be a radiative heater, such as an infrared heater. Such radiative heaters can utilize light in the visible spectrum and/or light in the non-visible spectrum (e.g. infrared) or a combination thereof. Such heating elements can include, but are not limited to, heat lamps and quarter elements. In some embodiments, the system utilizes one or more radiative heaters that are positioned to melt an exposed surface of a frozen product to be sampled by a manual or automated sampler.

B. Sampling Media

Sampling media is one fundamental aspect of the sampling device. Sampling media that is used to fabricate the sampling cover or sleeve needs to transfer the melted surface material without contaminating the energy source unless the energy source is single use as might be the case for the chemical packets. The media will generally be a food contact material for most applications, but other materials may be appropriate for non-food applications. For food application polyolefin materials such as non-woven polypropylene fabric would be appropriate. Sonic welding can form a wide range of sleeves for covering the heating element. The probe and cover shapes can be as simple as an open bag to something with appendages more like a glove. The configuration can be defined by the surface irregularities of the material to be sampled. Cellulose materials can also be used to fabricate sleeves that are appropriate for food contact.

In some embodiments, to prevent contamination of the heating element, the sleeve can be lined with a material impervious to the melted liquid produced during sampling. In some embodiments, this liner is a plastic web. This material can also be approved for food contact, but any suitable material for a given application could be used. In some embodiments, the material is a polyolefins material, which are often preferred as these materials are easier to work with. Again, for non-food applications many more plastics webs become acceptable. In some embodiments, the inner lining can be attached to the sampling sleeve media or just inserted depending on the fabrication process.

C. Exemplary Heated Sampling Probe Devices

FIGS. 1-7 and 12 depict exemplary heated sampling probe devices, in accordance with embodiments of the invention. These heated sampling probe device can be used in particular for aggregating sampling as described herein. It is appreciated that these probe devices are merely examples and that variations can be made to each in keeping with the inventive concepts herein.

FIG. 1 depicts a heating sampling probe device 100 defined as a glove 111 that includes an interior pocket 112a for receiving a hand of the sampling personnel. The glove includes a resistive heating element 120. An outer sampling cover 110 fits over the glove and heating element 120. The cover is fabricated from an absorptive sampling medium suitable for sampling a food product. The cover is defined with a pocket 112b to receive a hand of the user or to receive a tool (see FIGS. 2-3 for example). In this embodiment, the cover resembles a mitten where the pocket is slipped over the glove or hand of the user to faciliate sampling. The cover can include an interior liner that is impervious to fluid to protect the heating element and internal glove from any liquids. The resistive heating element 112 is a flexible element that extends across the fingers of the glove and is electrically coupled to control unit 122 having a thermostatic controller 123 to maintain a suitable elevated temperature and is powered by a power source 124. The power source 124 can be an external power grid or a portable battery, as described herein.

Figure 2:
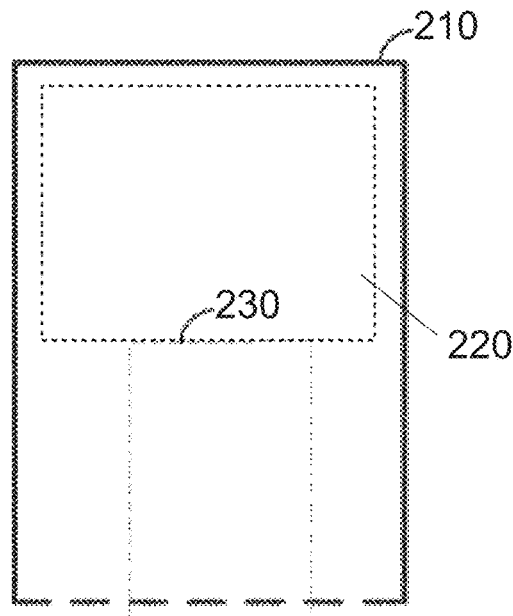
FIGS. 2-7 show alternative heated sampling probe devices, in accordance with some embodiments.
Figure 2:
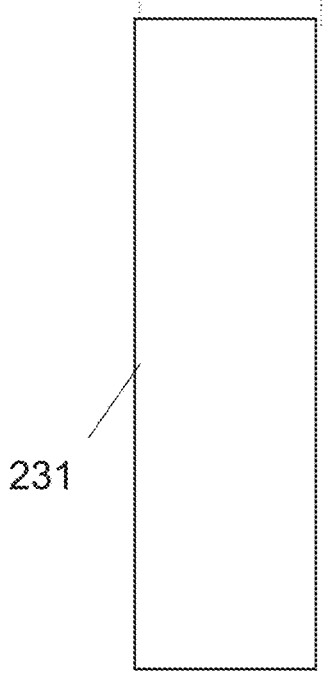

FIG. 2 depicts illustrates an heating sampling probe device 200 for aggregating sampling that includes a cover 210 having a pocket in accordance with aspects of the present disclosure. As shown, the cover 210 is made of a microbial sampling material and is formed such that it includes a pocket to receive probe tool 230 having a heating element 220 mounted on a distal end thereof. The probe tool 230 includes a shaft that extends proximally to a handle 231 to facilitate handling of the probe by the sampling personnel. It is appreciated that the tool and handle configuration can be utilized in any of the probe devices in FIGS. 2-7. In some embodiments, the probe tool can further include controls for controlling heating, or turning heat on/off and can further include a digital readout of the probe temperature during sampling.

Figure 3:
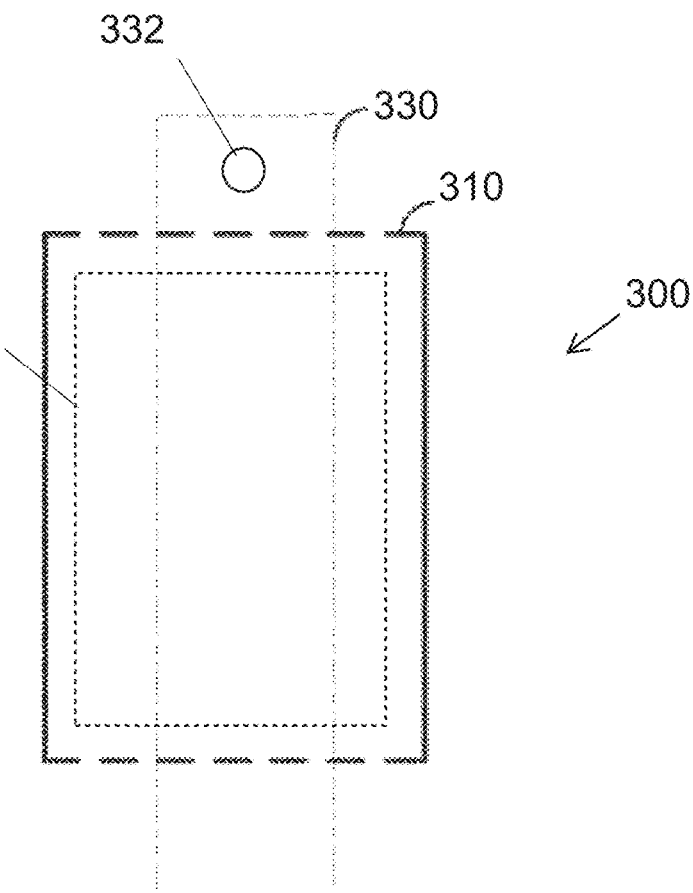

FIG. 3 illustrates another heated probe device 300 that extends through a cover 310 in accordance with aspects of the present disclosure. The cover 310 is formed of a microbial sampling medium and includes a pocket or opening extending therethrough. In this embodiment, the probe tool 330 extends distally of the cover and includes a hole 332, which can be used to store the probe when not in use and/or can be used to weigh the cover while on the probe after sampling.

Figure 4:
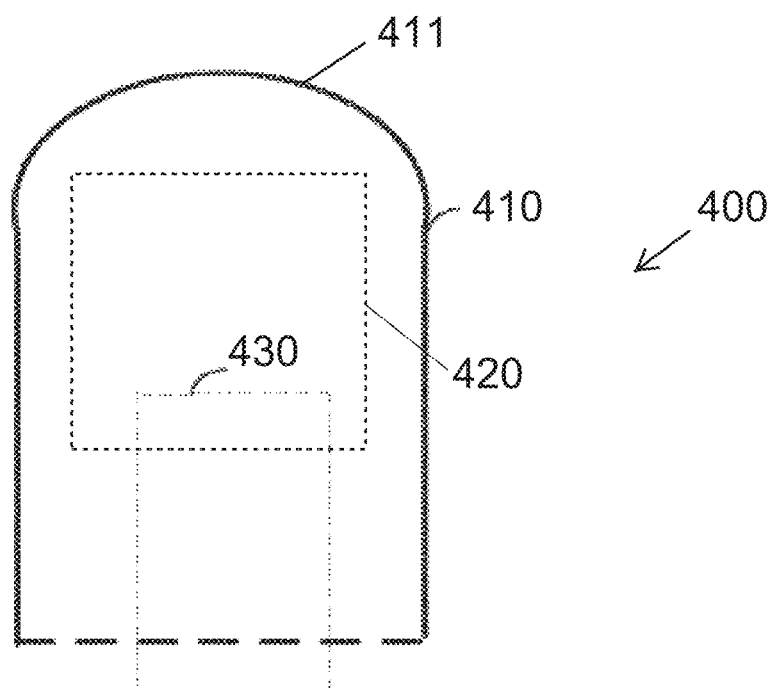

FIG. 4 illustrates another heated probe device 400 that includes a probe 430 having a heating element 420, with the probe being shaped so that the distal end has at least one convex surface 411. This configuration may be suited for sampling frozen product of a particular shape. As in previous embodiments, the probe includes a cover 410 with a pocket that fits over the probe with the heating element 420 mounted thereon.

Figure 5:
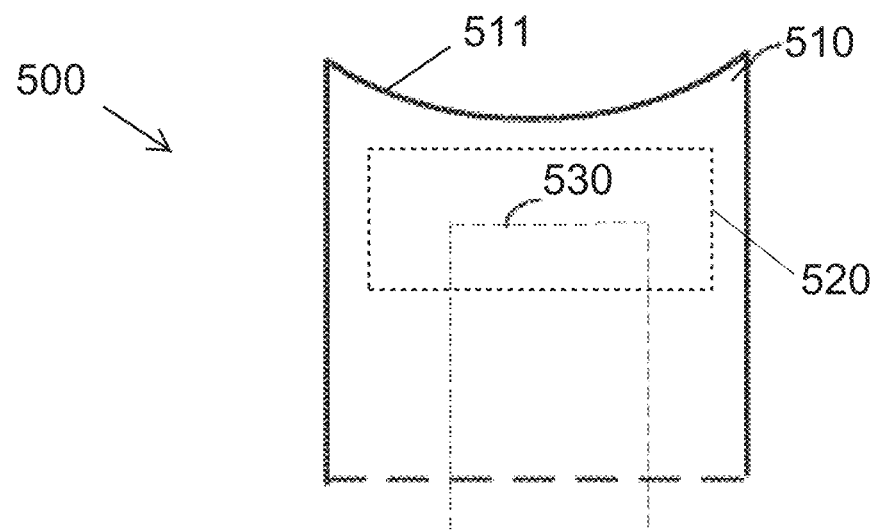

FIG. 5 illustrates another heated probe device 500 that includes a probe 530 having a heating element 520 mounted thereon, with the probe being shaped with a distal end having a concave surface 511. This configuration may be suited for sampling frozen product of a particular shape. As in previous embodiments, a cover 410 having a pocket fits over the probe with the heating element 420 mounted thereon.

Figure 6:
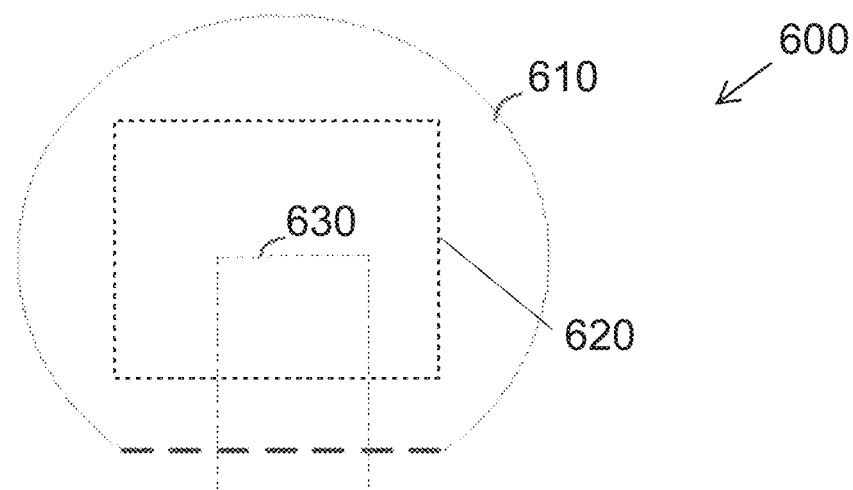

FIG. 6 illustrates another heated probe device 600 that includes a probe 630 having a heating element 620 mounted thereon, the probe having a rounded shape. This configuration may be suited for sampling frozen product of a particular shape. As in previous embodiments, a cover 610 having a pocket fits over the probe with the heating element 520 mounted thereon.

Figure 7:
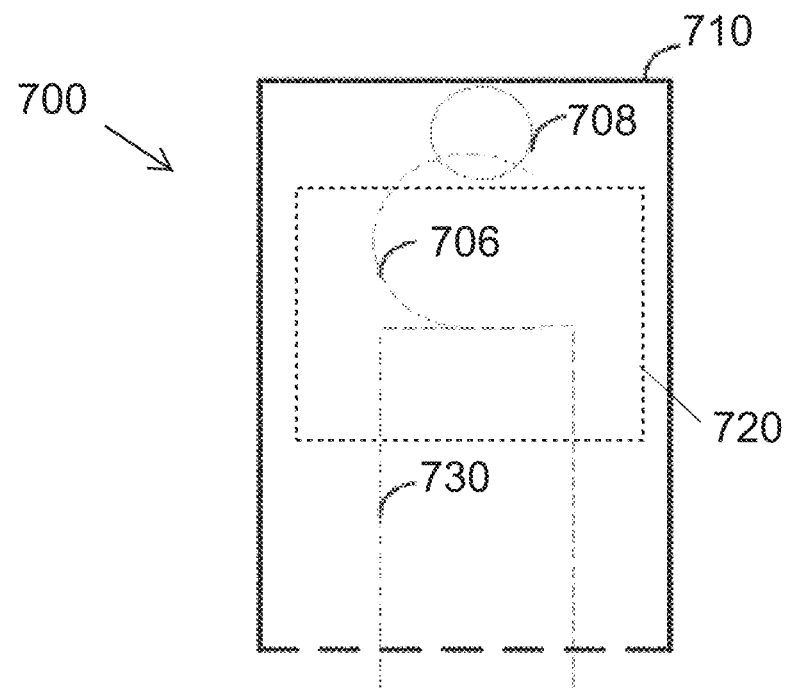

FIG. 7 illustrates another heated probe device 700 that includes a probe 730 having a heating element 720 mounted thereon. As in previous embodiments, a cover 710 having a pocket fits over the probe and heating element 720. In this embodiment, the probe includes a coupling or retention feature for attaching the cover 710 to the probe. The cover 710 may include a hole or loop 708, such as positioned within the pocket of the cover 710 and attached to an inner surface of the cover. This hole or loop 708 may be used by a hook 706 of the probe 730 to attach to the cover 710. It is appreciated that various other coupling mechanism could be used on any of the embodiments herein. Alternatively, as in previous embodiments, retention of the cover on the probe may rely on the fit of the cover over the probe device.

Figure 12:
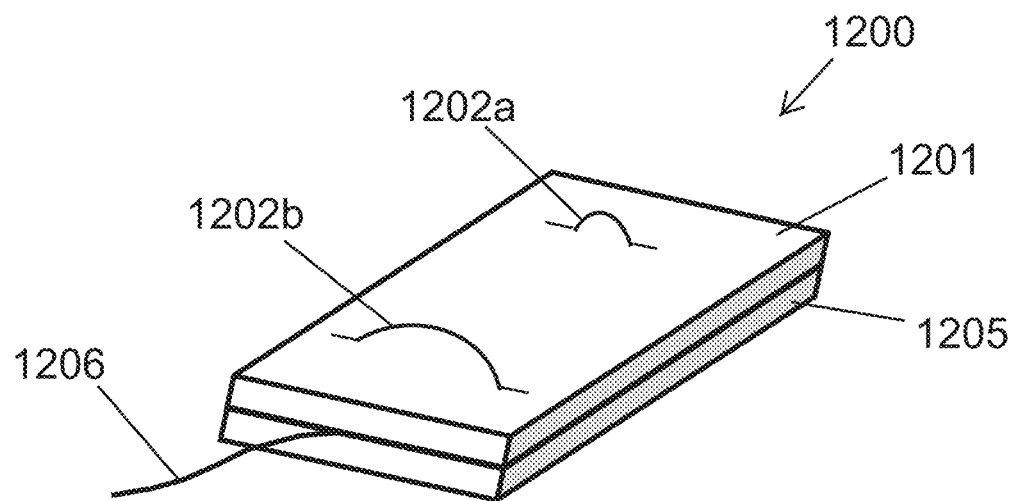
FIGS. 12-13 show a heated sampling device for manual sampling and an associated heating element in accordance with some embodiments.
Figure 13:
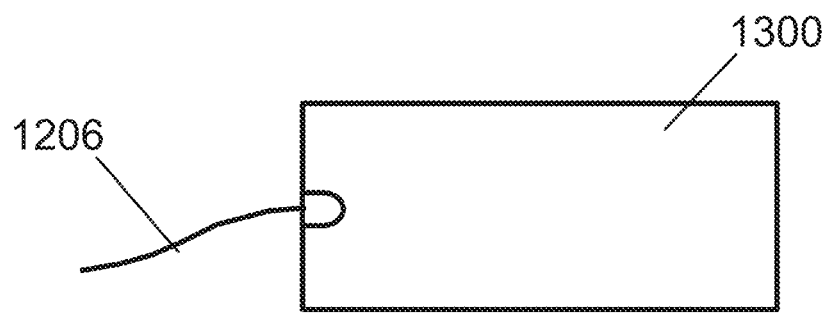

FIG. 12 illustrates another heated probe device 1200, which includes a base 1201, a conformable pad 1205 and a heating element (not shown) sandwiched therebetween such that the heatable probe is able to flex for modest contours in the surface to be sampled. In some embodiments, the pad may be cutout to allow the bulge in the heating element to fit without distortion of the sampling surface. Rubber cement or any suitable adhesive or attachment means can be used. A sample sheet or cover can be placed over the heatable probe, as described previously. The sample sheet or cover can be of any suitable absorbent material (e.g. a MicroTally mitt) to sample the surface being contacted. Further, the entire probe can be placed in a bag before being placed in the sampling cover to prevent contamination of the probe and the user's hand. In this embodiment, the base 1201 is made from a substantially rigid material (e.g. wood, plastic, metal) so as to allow the user to exert a suitable force through the base to the surface being sampled. The base 1201 can also act as an insulator to protect the user's hand from heat. The base can include attachment features 1202a, 1202b to facilitate attachment to the user's hand during sampling. By placing their hand through the wrist loop 1202b and finger loop 1202a, the user can readily position the sampling probe over the surface to be sampled and press the probe against the surface for a sufficient time to melt the surface for sampling. The loops can be formed of any suitable material (e.g. rubber, wire, cord) and attached to the based by any suitable means (e.g. knots, staples, etc.). In some embodiments, the loops can be adjusted for fit. The conformable pad 1205 can be foam or any compressible conformable material in order to better conform to uneven surfaces for improved sampling. In this embodiment, the base and conformable pad are rectangular and substantially planar in shape, however, it is appreciated that the base and conformable pad could be of any suitable size and shape, as needed for a particular application. A heating element (such as that in FIG. 13) is disposed between the base and conformable pad, the heating element being connected to an elecrical source through cable 1206. FIG. 13 shows an exemplary planar heating element 1300 that can be used in the heatable probe of FIG. 12. This heating element is rectangular, planar and relatively thin (e.g. ABN heater pad 4×5 inches), which lends itself to placement between the base and the conformable pad. In some embodiments, the heating element is controlled by a variable transformer, known as a Variac (e.g. YaeCCC 3 A Variac), that can be plugged into a standard 120-V outlet, which is rated for 500 W, more than suitable to handle the power requirements of the heating element. The temperature can be adjustable by use of the Variac that can reduce the voltage.

In some embodiments, the sampling protocol for such a probe is as follows. When a desired temperature of the probe is reached, the user slides their hand through the wrist loop and slides a finger through the finger loop. The user then inserts their hand and the probe into a bag (e.g. gallon bag) that is sterile on the outside or at least sanitary. The user then inserts their bagged hand with probe into a sample medium cover (e.g. MicroTally® mitt) and proceeds to sample, placing the probe on the frozen surface to be sampled and maintaining contact sufficiently to melt the surface and obtain the sample. The user's free hand can be used to avoid cord contacting food to be sampled. When sampling is complete, the sample cover is returned to the bag and a new gallon bag is replaced as would be done for a glove. In some embodiments, the bag extends further along the user's arm than the sample cover (e.g. by one or more inches) such that the user can simply grab the proximal end of the bag with their free hand and turn the bag inside out, thereby bagging the sample cover in the bag, which can then be sealed and sent for sampling. In such embodiments, the bag can have a length between 5 and 20 inches, preferably between 7 and 12 inches. In some embodiments, the bag can include a closure feature on a proximal end (e.g. embedded zip, tie, etc). This approach improves ease of sampling and prevent unintentional cross-contamination of the sample cover after sampling so as to maintain integrity of the sample.

II. Heated Sampling Methods

A. Sampling Methodology

As a validation step for aggregated sampling, a before and after weight of the sampling sleeve or media is obtained in order to determine the weight of material during the sampling process. Care must be taken to avoid other changes in the weight, for example, changes due to a tear off strip for the bag. In many cases, the automation of the manufacturing process will provide a consistent before-sampling weight such that an after-sampling weight is sufficient to ensure that the sampling was properly executed. This is of particular importance when the analyte is a negative attribute such as the presence or absence of pathogens. Too little weight gain would indicate too little material was transferred during sampling. While this aspect is described within the context of heating sampling, it is appreciated that this aspect can be utilized to ensure sufficient sampling was collected in any type of sampling, particularly aggregate sampling (e.g. stationary samplers, non-heated sampling, etc.).

In some embodiments, the system can include a means to weigh the sample immediately after sampling. For example, in a cart mounted system, a scale could be provided for weighing the sample media directly after sampling. In some embodiments, the system is configured to readily indicate whether the weight is indicative of a suitable sampling, for example by an indicator (e.g. audio or visual alert). In some embodiments, the scale or system includes the pre-set before sampling weight of the sampling media. In some embodiments, the before-weight can include the weight of other components, such as the sampling tool. Thus, this allows the technician to place or hang the tool with the sampling media on the scale and immediately determine whether a suitable sample was obtained or whether the sampling media needs to be re-applied to the product being sample. In such case, care must be taken to avoid contamination of the sample from the scale and/or cross-contamination of the sample from the scale, for example, by use of disposable sheets or liners placed on the scale. In some embodiments, the scale could include a specialized feature that interfaces with a portion of the sampling media or tool (e.g. a hook that interfaces with a hole on the sampling media or tool), thereby allowing for weighing of the sampling media without contamination of a conventional scale surface.

In sampling, it is critical to avoid contamination. Contamination is always related to the planned testing or the analytes. Generally, one avoids contact with surfaces other than the material to be sampled. For microbial testing, this means that aseptic technique is used. It also means that the sampling sleeve must be hygienic relative to the organisms to be tested. As a practical matter, this usually implies that the sampling sleeve is sterile. Sterilization can be achieved in any suitable manner, which can include use of chemicals such as ethylene oxide, radiation such electron beams, or heat. Other techniques may be appropriate in particular instances. The operator or user will almost certainly be wearing gloves while using the sampling device. Protecting the material and the sampling sleeve from contact with the operator is an important part of preventing contamination. In some instances, other protective equipment can be used as appropriate.

Given that this sampling technique depends on various differential temperatures between the sampling surface of the sampling device and the material to be sample, it can be beneficial to temper the product to reduce the specific heat requirement to achieve surface melting. Expressed differently, the sampling is easier and quicker if the surface of the material to be sampled is closer to the melting point than if the material is much colder. Thus, in the beef trim example described below, the frozen trims have been removed from the $-20°$ C. storage for several hours so that the surface temperature rise while the bulk of the product remains much colder.

Figure 8A:
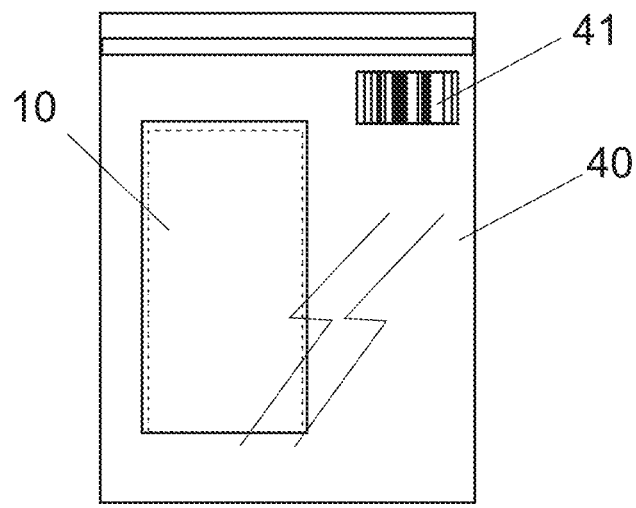
FIGS. 8A-8E depict an exemplary sampling procedure with a heated sampling probe, in accordance with some embodiments.
Figure 8B:
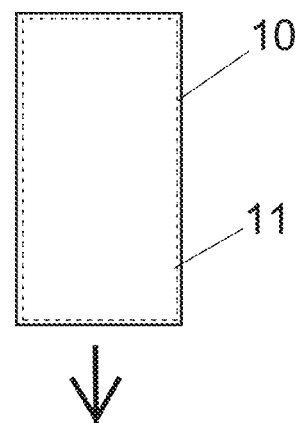
Figure 8B:
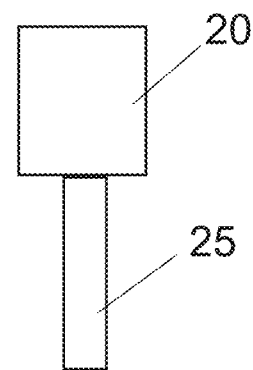

To further illustrate this sampling technique, a sampling procedure, in accordance with embodiments of the invention, is illustrated in FIGS. 8A-8D. In order to proceed with a requested sampling of a frozen or solid product, a user obtains a sterilized cover 10 in a sealed back 40, as shown in FIG. 8A. As described previously, the cover is fabricated from a suitable microbial sampling medium. The user identifies the sampling cover by reading or scanning an identifier 41 (e.g. barcode) on the bag. The sample identifier can be entered or received into an automated or computerized sample tracking system. The user then removes the sterilized cover 10 and places it over onto the heated sampling probe having a heating element 20 mounted thereon. The cover includes an internal liner 11 that is impervious to fluid. The heating element 20 can be configured in accordance with any of the approaches described herein.

Figure 8C:
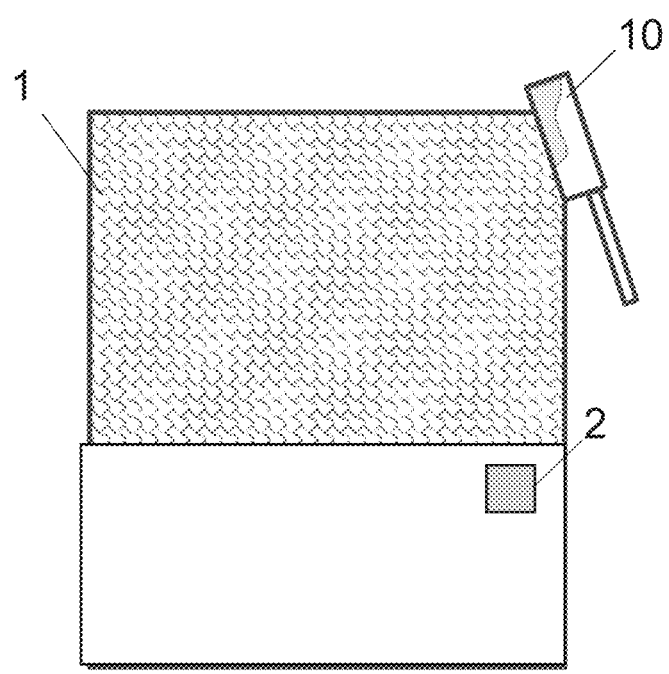

The user identifies the product (e.g. lot or batch) by reading or scanning an identifier 2 on the product or product packaging, as shown in FIG. 8C, and associating the identifier with the sample, by writing on the sample bag itself or by entering the sample identifier in the sample tracking system. Once the heated probe is heated sufficiently to an elevated temperature above the melting point of the product being sampled, the user then proceeds with the sampling protocol and contacts the cover 10 of the sampling probe to the surface of the product 1, as shown. For aggregating sampling, the user typically contacts the surface of the product at multiple locations and/or sweeps the probe across a large surface of the product to ensure the sample is an aggregate sample that is representative of the product being sampled.

Figures 8D, 8E:
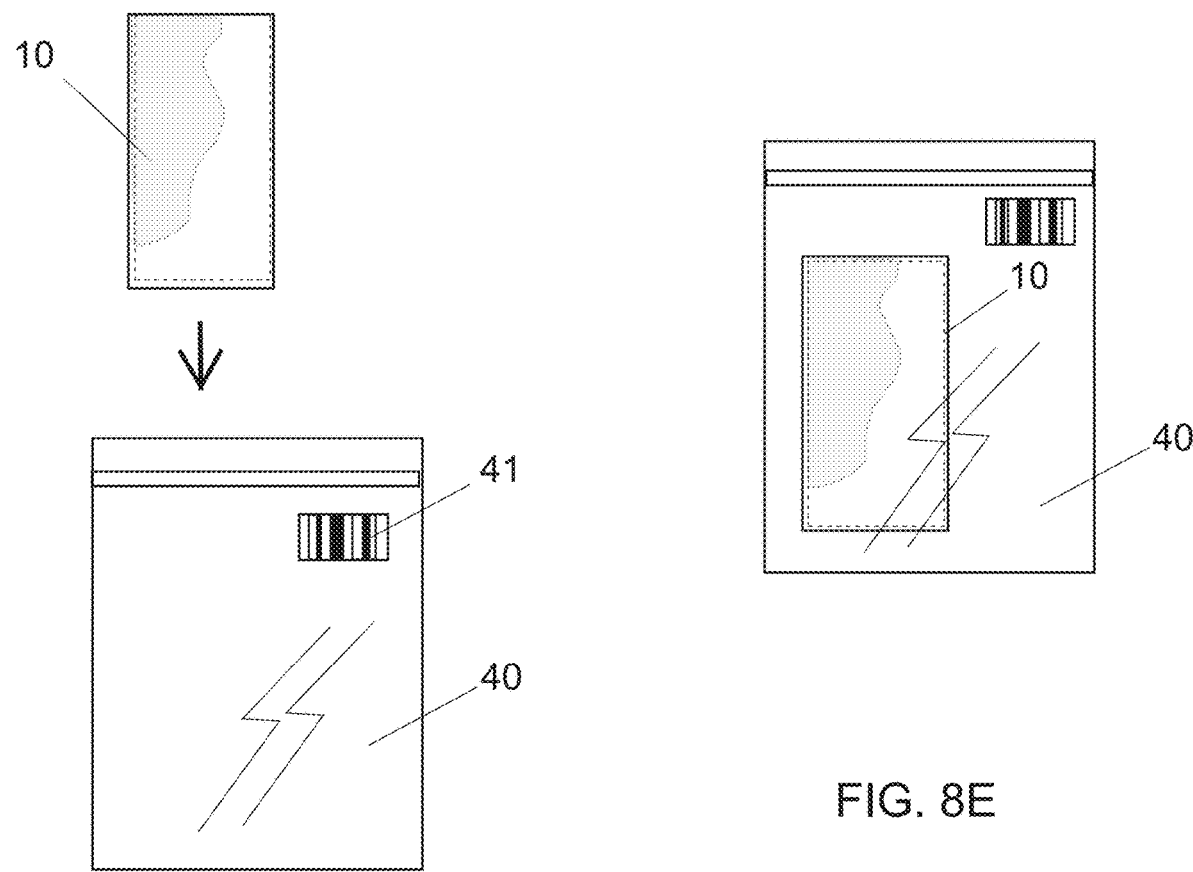

Once the sampling has been performed according to the designated sampling protocol, the user then removes the cover 10 from the probe and places the cover back into the sample bag 40, as shown in FIG. 8D. In some cases, the user can ascertain that sufficient sample is likely to have been collected by the wetted appearance or staining of the cover 10. The user then seals the cover 10 within the bag, as shown in FIG. 8E, which can then be weighed and compared to a before-sampling weight (either a standard or measured weight) to verify that sufficient weight of liquid sample has been collected. The sample can then be tested according to any appropriate testing method. In some embodiments, the sample can be tested by a procedure that extracts and concentrates the liquid sample for direct testing of the analyte of interest without any enrichment procedure.

Figure 9:
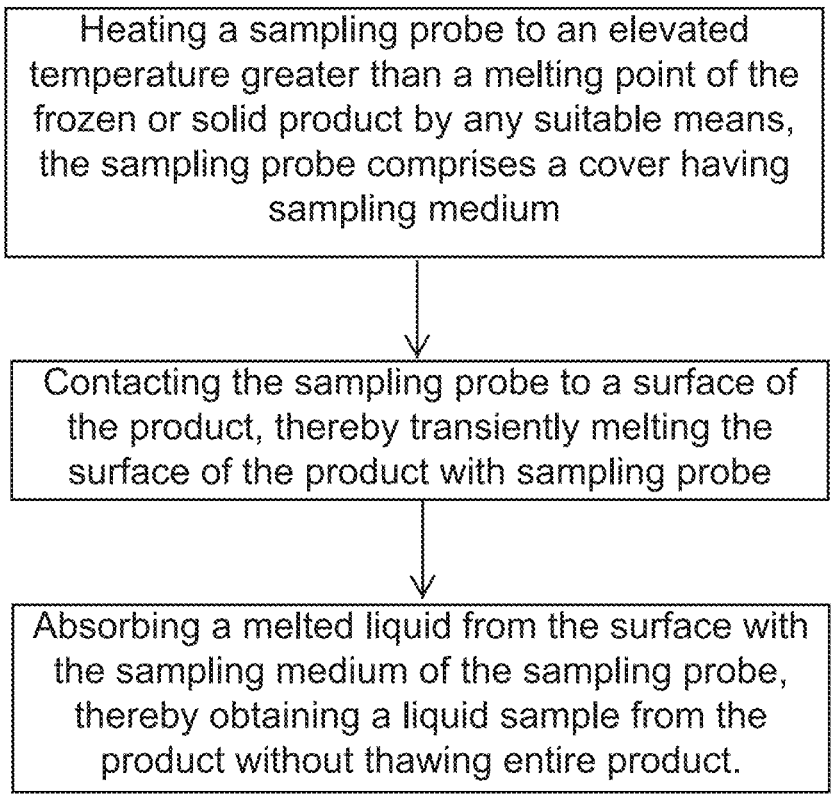
FIGS. 9-11 depict methods of sampling and testing, in accordance with some embodiments.
Figure 10:
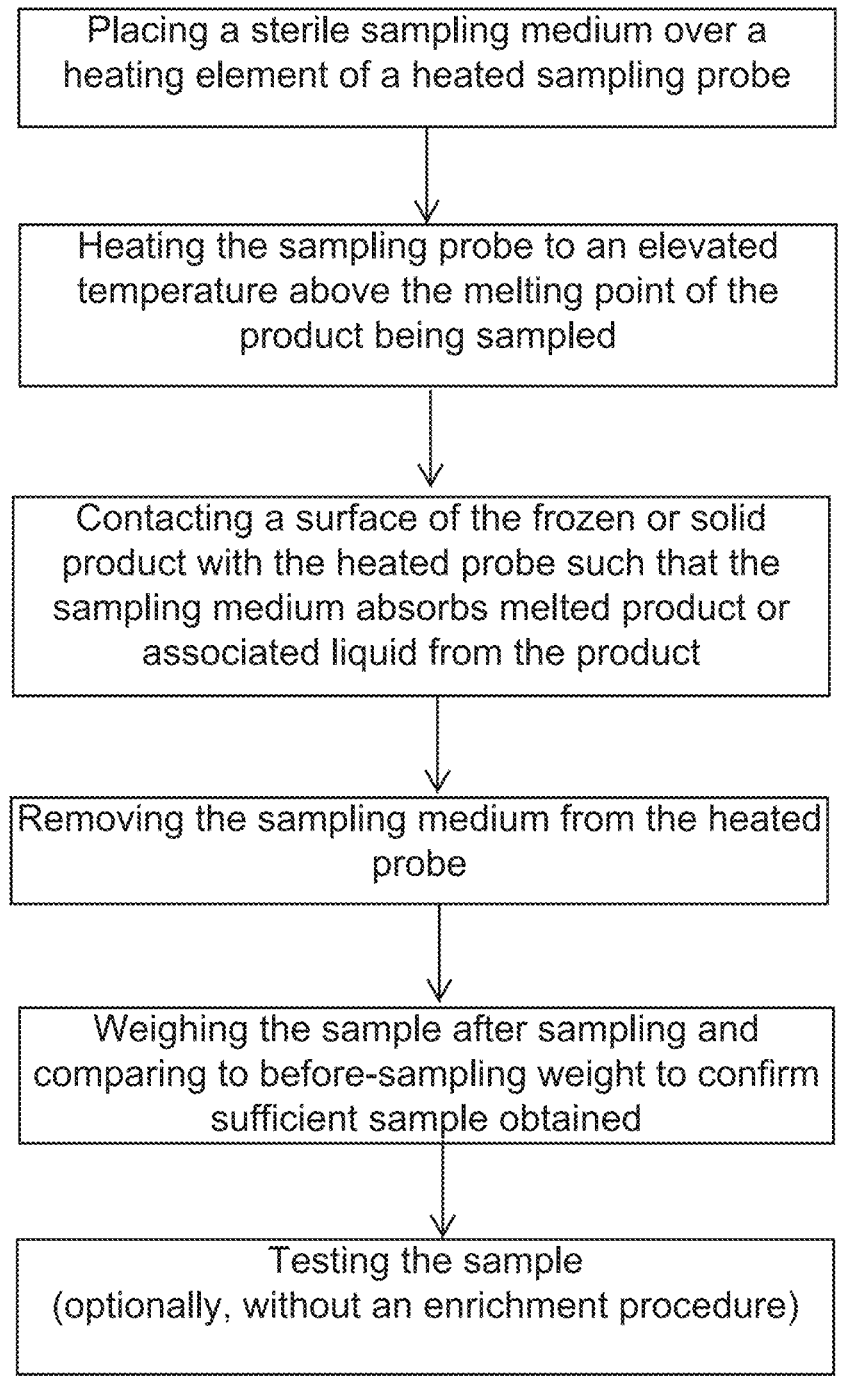

FIGS. 9-10 depict example methods in accordance with aspects of the invention. It is appreciated that the particulars of these steps may vary and that these methods can include any number of intervening steps or additional steps as desired.

FIG. 9 depicts an example method in accordance with aspects of the invention. The method includes steps of: heating a sampling probe to an elevated temperature greater than a melting point of the frozen or solid product by any suitable means, the sampling probe having a cover fabricated of sampling medium; contacting the sampling probe to a surface of the product, thereby transiently melting the surface of the product with sampling probe; and absorbing a melted liquid from the surface with the sampling medium, thereby obtaining a liquid sample from the product without thawing entire product.

FIG. 10 depicts an example method in accordance with aspects of the invention. The method can include steps of: placing a sterile sampling medium over a heating element of a heated sampling probe; heating the sampling probe to an elevated temperature above the melting point of the product being sampled; contacting a surface of the frozen or solid product with the heated probe such that the sampling medium absorbs melted product or associated liquid from the product; removing the sampling medium from the heated probe; weighing the sample after sampling and comparing to before-sampling weight to confirm sufficient sample obtained; and testing the sample (optionally, without an enrichment procedure).

Figure 11:
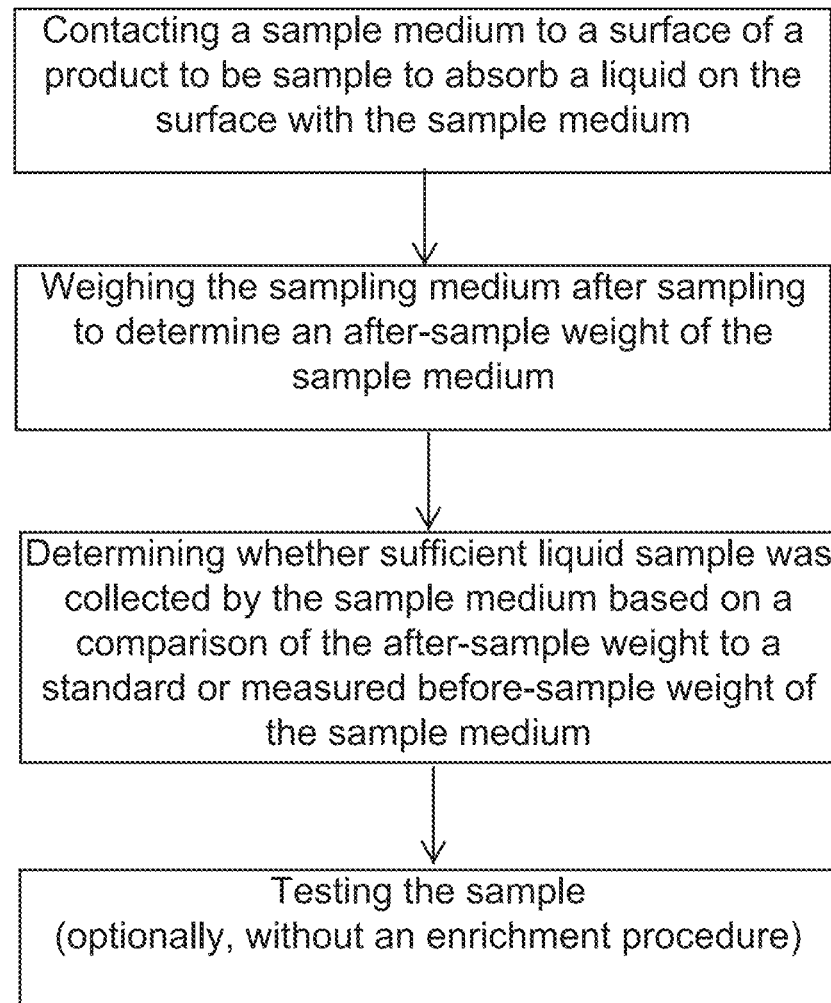

FIG. 11 depicts an example method in accordance with aspects of the invention. The method can include steps of: contacting a sample medium to a surface of a product to be sampled to absorb a liquid on the surface with the sample medium; weighing the sampling medium after sampling to determine an after-sample weight of the sample medium; determining whether sufficient liquid sample was collected by the sample medium based on a comparison of the after-sample weight to a standard or measured before-sample weight of the sample medium; and testing the sample (optionally, without an enrichment procedure).

B. Examples

To further illustrate the invention, we describe here the application of the invention to testing frozen beef trims for the presence of human pathogens. Given the novelty of this approach, it does not yet have regulatory approval. As such, adjustments of the sampling methods and device described herein can be expected to comply with regulatory requirements. Nevertheless, variations are in keeping with the inventive concepts described herein.

In one example, to prepare for sampling a lot of beef trims, various supplies need to be prepared. These supplied include the bagged and bar-coded sampling sleeves, the heating system, a scale, and electronic devices for documenting the tracking of samples. A trained operator with appropriate gloves and appropriate cold room clothing is also needed. A working area to facilitate the sampling is also helpful. And finally, a work order is typically prepared, such as by a computerized sample tracking program, that requests the item and quantity (e.g. 7 boxes) to be sampled.

As the sampling process starts, 7 fifty-pound boxes are transferred from the cold storage freezer at −20° C. to a tempering area nearer a melting point (e.g. about 4° C.) for testing. After tempering for a suitable time, the operator scans the bar-code on the bag of the first sleeve using the application on his phone assigning it to the first sample. The peel off label from the sleeve bag is attached to the box linking this box to the sample in the event that follow up sampling or other action is warranted after the process is complete. And finally, the box and inner wrapping are opened exposing the beef trims for sampling.

The sampling sleeve is slid over the heating element of the sampling device, in this case the probe can be defined as a channeled silicon pad with metal reinforcing frame and handle, the heating element being preheated to 40° C. with circulating water with ethanol as an antifreeze. While circulating water as heating source it described here, it is appreciated that any suitable heating source could also be used. The wrapped probe is run slowly over the surface of the frozen beef trims sullying the sleeve with surface liquid from the trims. This surface liquid is where pathogens, if any, are expected given that the interior of the trims are essentially sterile with regards to pathogen presence. This process continues until the sleeve is suitably wetted ensuring a good sampling. In the case of beef samplings, the sampling medium will be well-colored or stained pink by contact with the beef trims so that the appearance of the sampling medium may indicate when a suitable sample has been taken. Therefore, in the case of beef trimming it may be useful for the sampling medium to be light in color (e.g. white) so that staining can be easily observed. Care is taken to access any accessible niches in the block of trims and reaching down the sides of the block as the packaging permits. This process can be timed and required to take at least a pre-determined duration (e.g. 3 minutes) to ensure adequate contact with surfaces of the product to ensure the aggregate sample is representative of the product.

After sampling, the sleeve is removed from the sampling probe and returned to the original bag without contacting the sleeve to avoid contamination. The probe is sanitized with alcohol to limit cross contamination risk. The process is repeats for samples 2 through 7. All seven cartons are then resealed and returned to the lot with their barcodes visible should they be needed. This sampling is considered non-destructive as the quality of the product is unchanged for its intended use.

At this point, the bar-coded samples are taken to the test site where they are weighed to ensure that sufficient material has been extracted from the sample. In other embodiments, the samples could be weighed during or immediately after sampling at the testing sight. The weight of sleeves in bags is consistent enough that a constant tare weight provides sufficient precision for this determination. Samples that are underweight are not considered valid for negative findings and need to be replaced. However, a positive result for any sample is deemed informative.

With weights attached to the sample record, the extraction procedure is performed within an analyzer (e.g STAR analyzer) which extracts and concentrates the sample sufficiently for direct molecular determination of the presence or absences of pathogens, generally O157 for beef. This testing approach can be utilized without enrichment, thereby greatly increasing the speed and efficiency of testing. For such testing, the sample tested should be an aggregate sample that includes surface samples obtained from multiple locations or moving the sample across a larger surface so that the results correspond to the entire batch or lot of product being samples. In one aspect, the use of aggregate sampling or an aggregating sampler may reduce the noise and as with the cross contaminations metrics, these ratios can be handled with statistical process control to look for deviations. This allows for sample testing that can be delivered in almost real time because the aggregating samplers collected enough cells for concentration and direct analysis without enrichment. Various aspects of this type of sampling can be further understood by referring to U.S. Patent Publication No. 2019/0049419 entitled "Method and Apparatus for Applying Aggregating Sampling to Food Items" filed Aug. 7, 2018, which is incorporated herein by reference: any of the sampling or testing aspects described therein can be utilized in testing of samples obtained by the heating sampling methods and system described herein. It is appreciated that the above method can be utilized to obtain surface sample for any suitable type of testing. These results can be reported to the FSQA data management system to allow for the proper disposition of the lot. Pathogen positive lots need to be directed to commercial cooking processes.

In another example, authentication of apple juice concentrate is examined. Apple juice can be adulterated with a variety of sugar syrups that can only be detected by specialized procedures. High quality apple juice is generally stored under frozen conditions. It would be desirable to confirm the authenticity of the product without the need to thaw several boxes of the product. Thus, the sampling methods and devices described herein can be also be applied to quality testing of a frozen product, such as apple juice concentrate.

In this example, the sampling procedures are similar. The processing need not be aseptic but still contamination needs to be avoided. Heated sleeves are used to collect the surface melt of the concentrate. This melt is extracted into water and dried under nitrogen. The residue, mostly sugars and other carbohydrates is derivatized for gas-chromatographic analysis of the complex carbohydrates looking for the finger prints of materials such as hydrolyzed inulin syrups. The ratio of juice constituents will also need to fall within the norms. In this way, apple juice concentrate can be authenticated without a full thaw.

In yet another example, a hard glassy epoxy resin is sampled for characterization. The resin is hard at room temperature but becomes quite fluid at 75° C. . A sampling temperature of 85° C. is selected as high enough to allow transfer of a surface portion of the resin to the sampling sleeve. At these temperature, additional thermal protection is required for the user to avoid scalding. Again aseptic technique is not required. The sleeve is allowed to cool in air without returning to a bag. The cooled sleeve is analyzed by attenuated total reflectance (ATR) infrared spectroscopy to confirm the identity and purity of the resin.

III. Heated Sampling Systems

In another aspect, the invention pertains to systems that further facilitate heating and/or sampling of frozen food products. These approaches increasingly allow for automation of one or both of heating and sampling, thereby reducing reliance on the user, which may increase consistency of sampling and reduce the burden on workers in regard to sampling.

Figure 14:
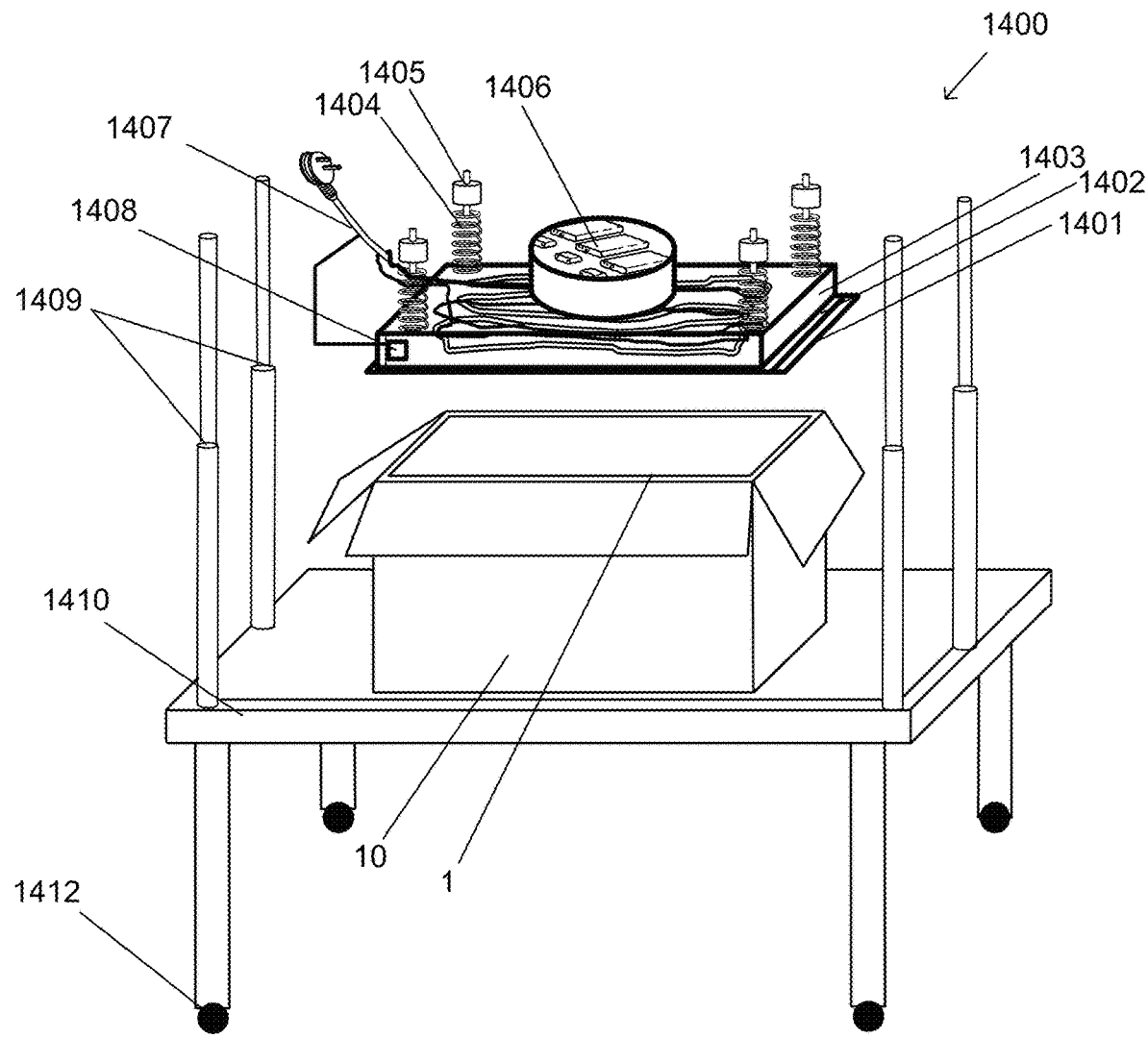
FIG. 14 shows a heated sampling device for automated sampling in accordance with some embodiments.

FIG. 14 illustrates an automated head sampling system 1400 that includes integrated heating and sampling features. System 1400 samples the exposed thawed surface of frozen food products 1 with a sampling medium 1401 (e.g. sampling sheet, sampling cover, MicroTally Swab) that is disposed on a movable assembly 1402-1406 that both heats and engages the sampling medium 1401 against the exposed surface of the product being sampled. The assembly includes a heated sampling plate 1403, on which the sampling medium 1401 is mounted with a plastic liner 1402 in between to protect and prevent contamination of the sampling plate. If used, the liner should be changed between samples. In this embodiment, the heated sampling plate 1403 is formed of a material that is heat conductive and elastic with a soft surface material. The heated sampling plate has built-in heating elements and a thermo-sensor controller to maintain an optimal sampling temperature for a given sampling procedure. The assembly can further include pressure springs 1404, vibration dampeners 1405, and a vibration motor assembling unit 1406, which imparts vibration to the sampling plate to improve sampling. It is appreciated that in some embodiments, the system could be configured without vibration capabilities and merely press the sampling medium against the exposed surface without vibration. The heating element power strip 1407 is controlled by thermo-controller 1408. The adjustable frame 1409 facilitates movement of the assembly downward to engage the sample plate to the exposed product surface. The adjustable frame can utilize any suitable means, typically hydraulic pillars that provide vertical movement of the assembly to lower the heat-sapling plate to press the sample plate against the frozen product surface. The entire system can be mounted on a mobile station or cart 1412 so that the system can be moved to differing locations in a given production line or moved between processing lines or different facilities with ease. In one aspect, during sampling, the product can remain in the packing box 10, which is placed on the sampling station surface 1410. After sampling, the box 10 can be removed and closed and the thermal mass of the remaining product will rapidly refreeze the exposed surface portion that was thawed during sampling. The next box of product can then be opened and placed on the sampling station surface for sampling. This approach minimizes disruptions in process workflow and maintains integrity of the product.

Figure 15:
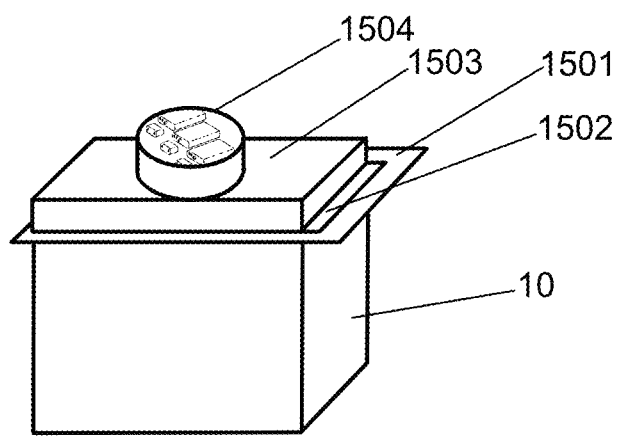
FIGS. 15 and 16 show sampling components for an automated heated sampling device in accordance with some embodiments.
Figure 16:
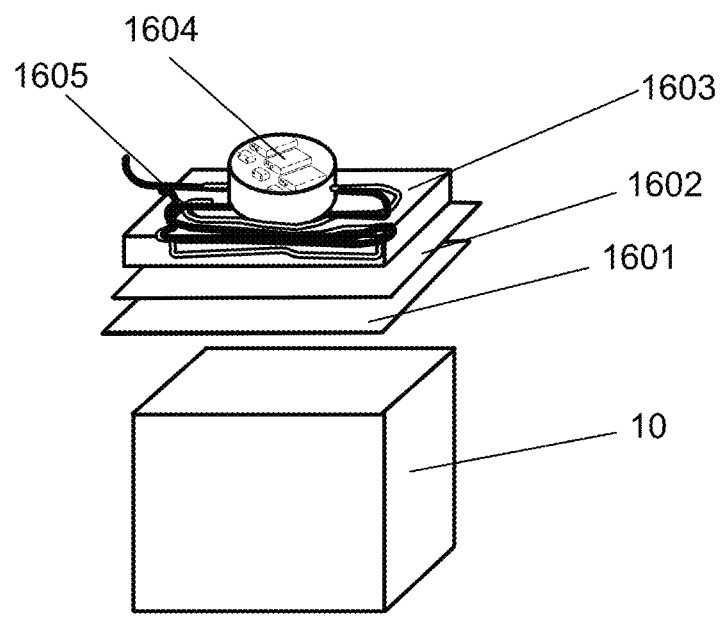

It is appreciated that various features of the system described above could be used separately or integrated within various other processing systems. In some embodiments, the sampling protocol can utilize other means to thaw the exposed surface of the product, for example, the ambient room temperature (e.g. a heated room), heated air blown on the surface, or radiative heating. In such embodiments, sampling can utilize an assembly with a sampling plate 1503 and vibration motor 1504 and a sampling medium 1501 with liner 1502 mounted on the plate, as shown in FIG. 15. This vibration plate can be placed on the exposed thawed sampling surface, either manually or robotically. In other embodiments, the assembly of the heated vibration sampling plate 1603 having a vibration motor 1604 and heater 1605 and having mounted thereon a sampling medium 1601 and liner 1602 can be provided separately, as shown in FIG. 16, and placed on the exposed frozen surface, either manually or robotically, to facilitate both thawing and sampling.

Figure 17:
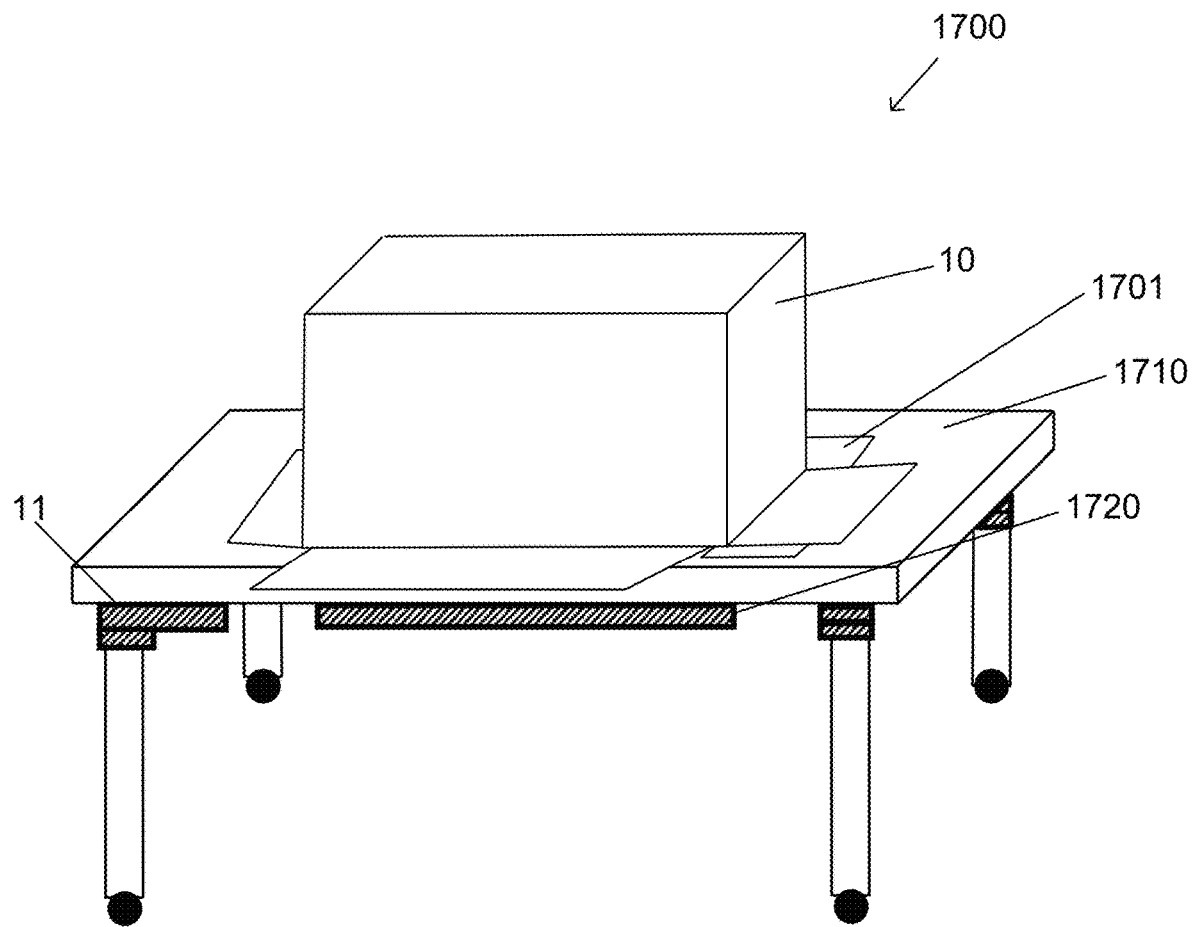
FIG. 17 shows an automated heated sampling device that utilizes vibration in accordance with some embodiments.

FIG. 17 shows another embodiment 1700 in which the sampling system includes a heated vibration plate 1710 that includes a vibration motor 1711 and a thermally-coupled heater 1720. The plate further includes a removable/replaceable sampling medium 1701 mounted thereon. A box 10 of frozen product is opened and flipped onto the sampling medium on the heated vibration table, and the plate is heated and vibrated for a sufficient amount of time for the exposed surface of product to thaw for sampling with the sampling medium. In some embodiments, the system can monitor, display and/or record a given weight pressure of the product on the table, which can be used to ensure sufficient sampling. After a suitable time has elapsed, the box is flipped back over and closed, the sampling medium is removed and bagged for sampling. The plate can then be cleaned and sterilized before the next sampling. Alternatively, a removable/replaceable liner can be used between the sampling medium and plate, as described previously. This design is simplified as compared to the previous system requiring a movable assembly, although the user is required to flip the each box before and after sampling, which may limit the size and weight of boxes that can be handled by a given user.

Figure 18:
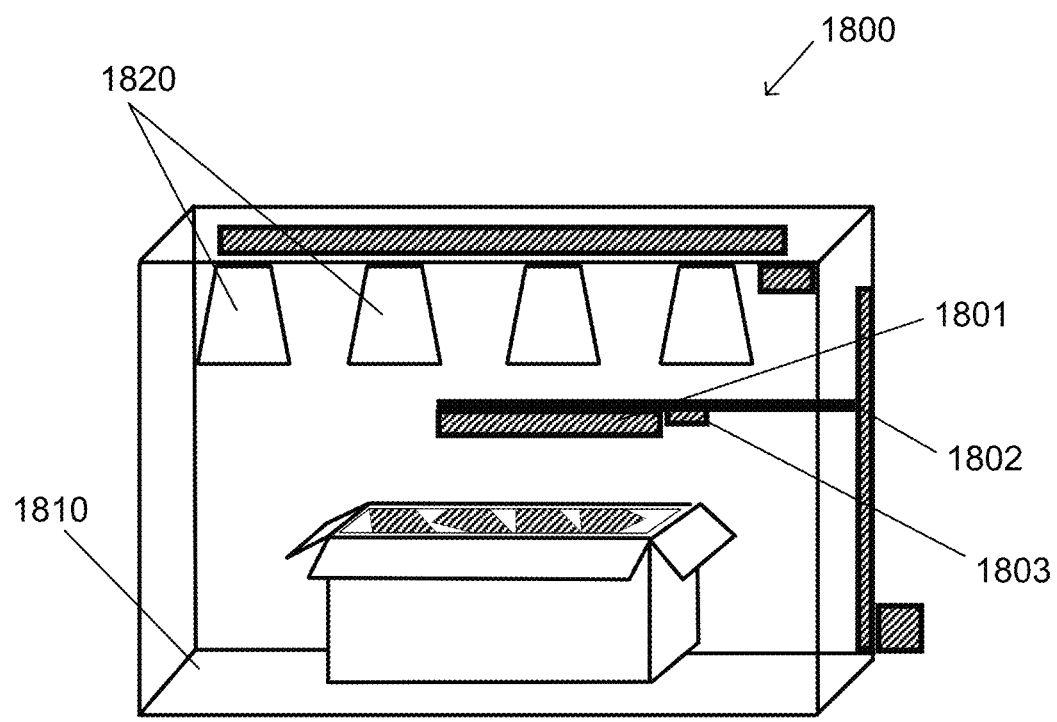
FIG. 18 shows a heated sampling system that utilizes radiative heating in accordance with some embodiments.

FIG. 18 shows another embodiment 1800 having one or more radiative heaters 1820, preferably an array of radiative heaters (e.g. heat lamps) that are suspended above the sampling station surface 1810 on which the open box of products is placed. Multiple radiative heaters can be spaced apart to provide more even, uniform heating temperature for consistent thawing of the exposed surface. In some embodiments, the system utilizes an array of heat lamps. In some embodiments, the system utilizes a quartz heater, which can better provide a linear source of heat over the product. The open box of product is allowed to remain under the radiative heater(s) for a suitable period of time (e.g. 1-20 minutes, typically 3-8 minutes) until the exposed surface thaws sufficiently to obtain a sample. In this embodiment, the sample medium 1801 is mounted on a movable assembly 1802 that presses the sampling medium against the thawed product to obtain the sample. In some embodiments, the system can include a temperature sensor 1803 that monitors and/or display the temperature of the surface of the product to ensure the product is sufficiently thawed for sampling. Temperature measurement can be by any suitable means, preferably by non-contact, such as by infrared in order to avoid contamination of the sensor. By this approach, the sampling procedure can be automated based on the temperature of the thawed product. In other embodiments, the user can monitor the temperature and/or apply the sampling medium (e.g. by hand or with a tool) to obtain the sample. It is appreciated that this temperature sensing aspect could be incorporated into any of the systems and/or probes described herein.

Figure 19:
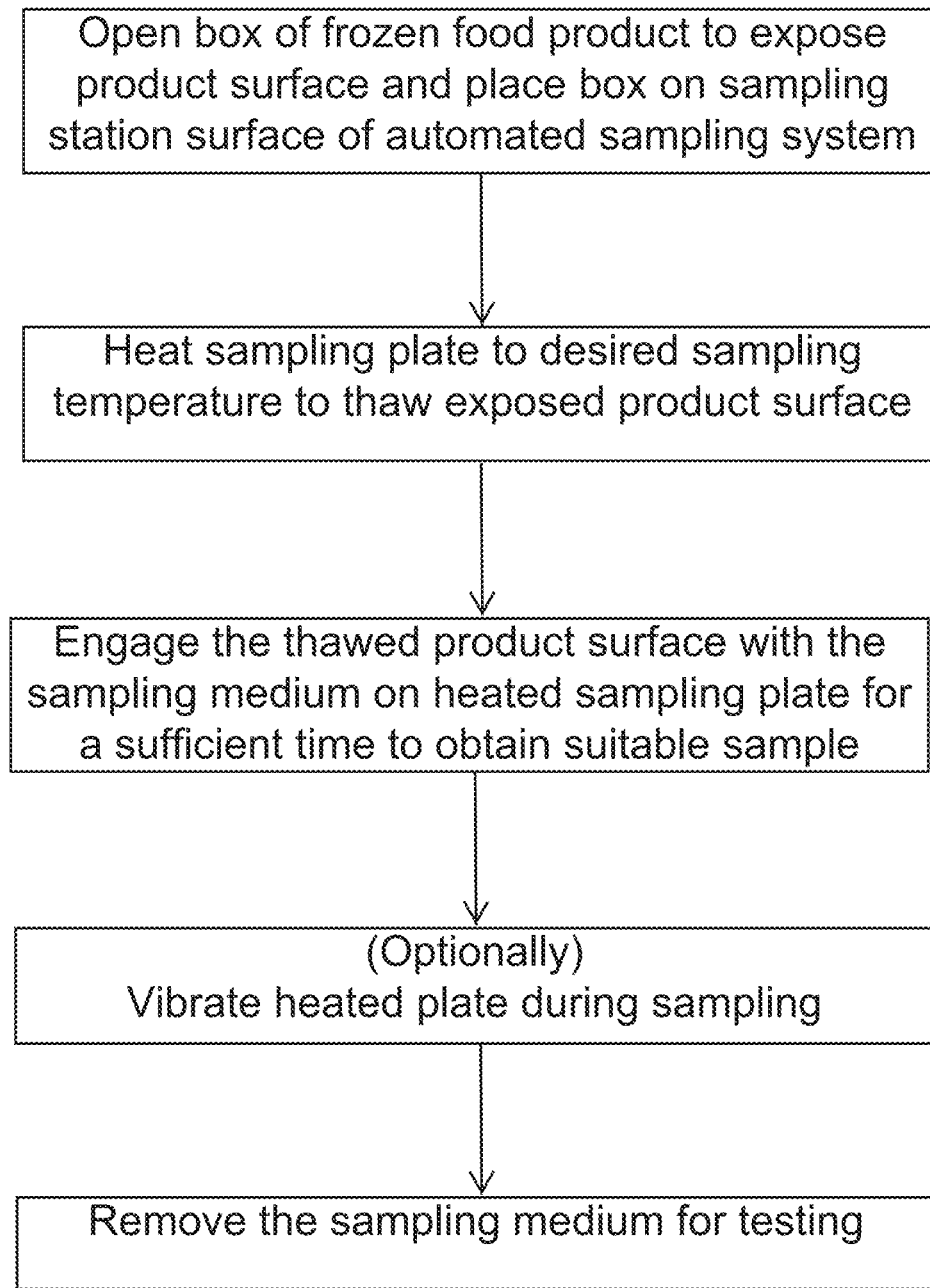
FIGS. 19-20 depict methods of sampling in accordance with some embodiments.
Figure 20:
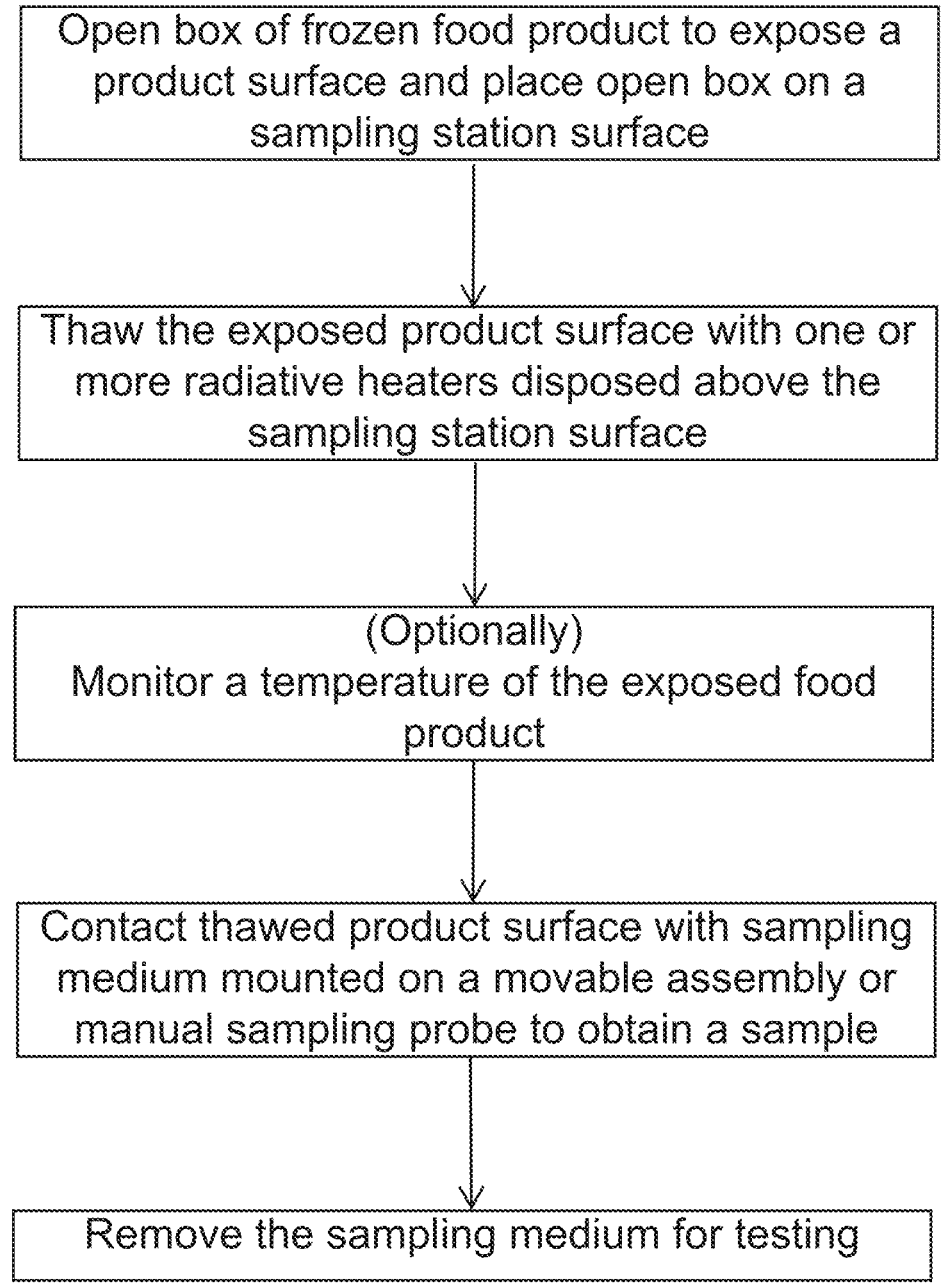

FIGS. 19-20 depict sampling method utilizing the sampling systems described above. Such method can include at least partly automated features in regard to heating and/or sampling.

As shown in FIG. 19, the sampling methods can include steps of: opening box of frozen food product to expose a product surface and place the box on sampling station surface of an automated sampling system; heating the sampling plate to a desired sampling temperature to thaw the exposed product surface; engage the thawed product surface with the sampling medium on heated sampling plate for a sufficient time to obtain a suitable sample; optionally vibrate heated plate during sampling; and remove the sampling medium for testing. Such a method can utilize the sampling systems shown in FIGS. 14-16.

As shown in FIG. 20, the sampling methods can include steps of: opening a box of frozen food product to expose a product surface and placing the open box on a sampling station surface; thawing the exposed product surface with one or more radiative heaters (e.g. heat lamps, quart elements) disposed above the sampling station surface; optionally monitoring a temperature of the exposed food product to ensure sufficient thawing before sampling; contacting the thawed product surface with a sampling medium mounted on a movable assembly or manual sampling probe to obtain a sample; and removing the sampling medium for testing.

In the foregoing specification, the invention is described with reference to specific embodiments thereof, but those skilled in the art will recognize that the invention is not limited thereto. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It is recognized that the terms "comprising," "including," and "having," as used herein, are specifically intended to be read as open-ended terms of art.

What is claimed is:

1. A sampling system for surface sampling of a frozen product, the sampling system comprising:
 a heater configured to be held over, on or near the frozen product, wherein the heater comprises one or more heating elements configured to heat to an elevated temperature above a melting point of the frozen product being sampled; and
 an aggregating sampler comprising a sampling medium, wherein the aggregating sampler is configured for manual surface sampling of the product after a surface is thawed by the heater by contacting the thawed surface with the sampling medium.

2. The sampling system of claim 1, wherein the sampling medium comprises an absorbent material so as to absorb a melted liquid produced from thawing the surface of the product with the heater.

3. The sampling system of claim 2, wherein the sampling medium comprises a pocket for receiving a hand or a tool to facilitate manual surface sampling of the surface of the product after thawing the surface.

4. The sampling system of claim 3, wherein the sampling medium comprises a mitten configured for receiving the hand of the user.

5. The sampling system of claim 1, wherein the sampling medium comprises a pad or fabric that is rectangular and substantially planar in shape so as to be conformable to the surface being sampled.

6. The sampling system of claim 1, wherein the sampling medium comprises a non-woven polypropylene fabric.

7. The sampling system of claim 1, wherein the aggregating sampler comprises a liner disposed on an underside or within an interior of a pocket of the sampling medium, the liner being impervious to a fluid produced by thawing the surface with the heater so as to prevent contamination of a hand of the user or tool within the pocket during manual sampling.

8. The sampling system of claim 1, wherein the heater comprises any of:
 a heated air blower for thawing the surface by heated air;
 a radiant heat source for thawing the surface by radiant heating; and
 a thermally conductive heat source for thawing the surface by heat conduction.

9. The sampling system of claim 8, wherein the heater comprises a thermally conductive heat source comprising a heated plate that is heated by resistive electric heating.

10. The sampling system of claim 1, further comprising:
a liner disposed over the heater, wherein the liner is impervious to a melted liquid from thawing a surface of the product with the heater so as to prevent contamination of the heater.

11. The sampling system of claim 1, wherein the sampling medium is integrated with the heater.

12. The sampling system of claim 1, wherein the heater and the aggregating sampler are used separately.

13. A method of sampling a frozen product, the method comprising:
thawing a surface of the frozen product with the heater of claim 1;
aggregate sampling the surface of the frozen product with the aggregating sampler of claim 1 after thawing of the surface with the heater.

14. The method of claim 13, wherein the sampling medium comprises an absorbent material so as to absorb a melted liquid produced from thawing the surface of the product with the heater.

15. The method of claim 13, wherein the sampling medium comprises a pocket for receiving a hand or tool to facilitate manual surface sampling of the surface of the product after thawing the surface.

16. The method of claim 13, wherein the sampling medium comprises a pad or fabric that is rectangular and substantially planar in shape so as to be conformable to the surface being sampled.

17. The method of claim 13, wherein the sampling medium comprises a non-woven polypropylene fabric.

18. The method of claim 13, wherein thawing the surface comprises any of:
blowing heated air from the heater;
exposing the surface to radiant heat from a radiant heat source of the heater; and
thermally conducting heat from a conductive heat source of the heater applied to the surface.

19. The method of claim 18, wherein the heater is a thermally conductive heat source that heats the surface by conduction, the heat source comprising a heated plate that is heated by resistive electric heating.

20. The method of claim 13, further comprising:
a liner disposed over the heater, wherein the liner is impervious to a melted liquid from thawing a surface of the product with the heater so as to prevent contamination of the heater.

21. The method of claim 13, wherein the sampling medium is integrated with the heater.

22. The method of claim 13, wherein the heater and the aggregating sampler are used separately.

* * * * *